United States Patent [19]
Burbury et al.

[11] Patent Number: 5,550,891
[45] Date of Patent: Aug. 27, 1996

[54] POSITIONING APPARATUS FOR X-RAY SOURCE

[75] Inventors: Robert L. Burbury, Elgin, Ill.; James W. Cutter, Hollister, Calif.

[73] Assignee: Olympic Controls Corp., Elgin, Ill.

[21] Appl. No.: 250,560

[22] Filed: May 27, 1994

Related U.S. Application Data

[63] Continuation-in-part of Ser. No. 850,891, Mar. 13, 1992, Pat. No. 5,469,492.

[51] Int. Cl.⁶ .................................................. H05G 1/06
[52] U.S. Cl. ............................................ 378/197; 378/193
[58] Field of Search .................................... 378/193–198

[56] References Cited

U.S. PATENT DOCUMENTS

D. 334,980   4/1993   Pritchard .
4,875,228   10/1989   Archer ...................................... 378/193

OTHER PUBLICATIONS

"Olympic Controls New Modular X–ray Systems"; Nov. 26, 1991; Fax New Letter; Olympic Controls Corp.; 1 page.

*Primary Examiner*—Don Wong
*Attorney, Agent, or Firm*—Leydig, Voit & Mayer, Ltd.

[57] ABSTRACT

An apparatus for supporting an X-ray source in a space having at least one wall and used for exposing patients to X-ray radiation, the apparatus comprising: an upright support member mountable adjacent to the wall; a slidably movable carriage supported by the support member and slidable thereto for planar movement in a plane parallel to the wall; a source assembly mounted to the slidable carriage, and adapted to receive the X-ray source, the source assembly including: a horizontally projecting base member fixed to the carriage; a horizontally extending tubular member pivotally mounted to the base member for pivotal motion in a horizontal plane; a stem receivably journalled within the tubular member for horizontal reciprocation with respect thereto; and a source attachment fixed to the source and including a collar journalled around the stem to provide rotational movement in a vertical plane about the stem.

14 Claims, 6 Drawing Sheets

POSITIONING APPARATUS FOR X-RAY SOURCE

CROSS-REFERENCE TO RELATED APPLICATIONS

This application is a continuation-in-part of application, Ser. No. 07/850,891, filed Mar. 13, 1992 now U.S. Pat. No. 5,469,492.

TECHNICAL FIELD

The subject invention is related to systems for operating medical X-ray equipment, such as that which is illustratively used in diagnostic or radiographic rooms.

BACKGROUND OF THE INVENTION

Conventional equipment for performing diagnostic X-rays on human patients comprises an X-ray source, usually a combination of an X-ray tube, a collimator, and various control mechanisms. The X-ray source generates and focuses X-rays. The patient is interposed between the X-ray source and an X-ray sensitive film, which is typically packaged in a cassette insertable into a holder.

The X-ray source and film holder are typically mounted on separate stands which allow the X-ray source and film to be manipulated and oriented with respect to patients of different sizes, and to allow X-rays to be taken of different parts of the body. Typically, a film holder for receiving an X-ray sensitive film cassette is mounted on a stationary stand. That stand includes siderails so that the film holder can be slidably vertically positioned along the stand. The X-ray source is also typically mounted on a stand for vertical motion. More specifically, an X-ray source may be mounted on a carriage which is adapted to slide up and down on a main column or tube stand. Accordingly, the height of the film and X-ray source can be adjusted by moving the respective vertically moveable carriages to the height which is appropriate for a particular patient or a particular exposure.

It is also necessary to adjust the distance between the film and the X-ray source. In the system described above, the tube stand for the X-ray source is mounted on a carriage. The carriage is adapted to slide back and forth along a track mounted in the floor, and the top of the tube stand travels along a rail, typically mounted to the wall. In this manner, the column along with the attached X-ray source may be moved in a horizontal direction so that the source may be set at the appropriate distance from the film.

In another type of prior art device, such as that disclosed in U.S. patent application Ser. No. 07/850,891, now U.S. Pat. No. 5,469,492 a wall-mounted frame for the X-ray source is stationary, and does not move horizontally. This frame does not include a central column, but rather includes spaced vertically extending side rails. A first carriage or tube slide is mountable on the side rails for vertical motion. This first carriage also includes top and bottom rails. A second carriage, to which the X-ray source is attached, is mountable on the tube slide for horizontal movement. Accordingly, vertical movement of the X-ray source is achieved by moving the tube slide on the side rails, and horizontal movement is achieved by moving this second carriage horizontally along the tube slide. A similar range of motion to the previously-described device is provided, but without the need for a floor-track, which may be undesirable for a variety of reasons.

Other prior art systems also exist which are adapted for use with a radiographic table. In a radiographic table, the X-ray film cassette is typically disposed underneath the table surface to allow X-rays to be taken of reclining patients. In such prior art devices, a stand similar to the latter one described above may be used. That is, a wall mounted frame includes side rails or other track means for receiving a tube slide which is moveable vertically on the stand. That tube slide, in turn, carries a second carriage which is horizontally moveable. In such a device, the radiographic table must be located in close proximity to the stand, since the X-ray source does not extend away from the second carriage to a great extent. This can be inconvenient in that the operator must often reach over the patient and the radiographic table for the purpose of adjusting the position of the X-ray source.

All the prior art systems just described include a support means for the X-ray source mounted adjacent to a wall. A slidably movable carriage or slide is supported on the support means such that this combination provides for vertical and horizontal translation of the X-ray source in a plane parallel to the wall for the purpose of properly positioning the source. While vertical and horizontal movement of the source are desirable, further ranges of motion for the X-ray source would also be desirable. For example, the possibility of moving the X-ray source vertically perpendicular away from and toward the wall would be advantageous. For the case of use of a radiographic table, such extension would allow the radiographic table to be placed a greater distance away from the stand upon which the source is mounted. This would lead to increased ease of movement both of the stand and of the reclining patient. Moveover, X-rays could be taken at a variety of positions away from the wall, wherein the same X-rays in prior art devices would need to be taken by means of moving the patient underneath the stationary X-ray source. With the X-ray source positioned away from the wall in this manner, the source could potentially become an obstacle to patients and medical personnel when not in use. Accordingly, another desirable range of motion for the X-ray source is rotation about a vertical axis so that the source, which normally extends away from the wall, could be folded to a position adjacent the wall.

An object of this invention, therefore, is to provide systems and assemblies for mounting X-ray equipment which allow for vertical and horizontal adjustment of an X-ray source, as well as additional ranges of motion. A further object of the invention is to provide such systems and assemblies which allow for such movement with a minimum of operator effort.

Another object of the subject invention is to provide systems and assemblies wherein all of the above-mentioned advantages are realized. These and other objects and advantages of the invention will be apparent to those skilled in the art upon reading the following detailed description and upon reference to the drawings and the dependent claims.

SUMMARY OF THE INVENTION

Those objects are achieved, in general, by utilizing certain new and useful assemblies for mounting an X-ray source. In accordance therewith, the subject invention provides for a source assembly for mounting an X-ray source, the assembly including a support means and carriage for providing movement of the X-ray source in a plane parallel to the plane of the mounting wall, the assembly comprising: a base member fixed to the carriage and horizontally projecting away from the carriage; a horizontally extending tubular member preferably square in cross-section pivotally mounted to the base member for rotation in a horizontal plane about the pivot point; a stem journalled within the tubular member for horizontal reciprocation with respect thereto; and a source mounting fixed to the X-ray source, the mounting including a collar journalled around the stem to provide rotational motion in a vertical plane about the stem.

The invention further provides for such mounting assemblies comprising various components to make operation smooth and reliable.

DETAILED DESCRIPTION OF THE PREFERRED EMBODIMENT

Figure 1:
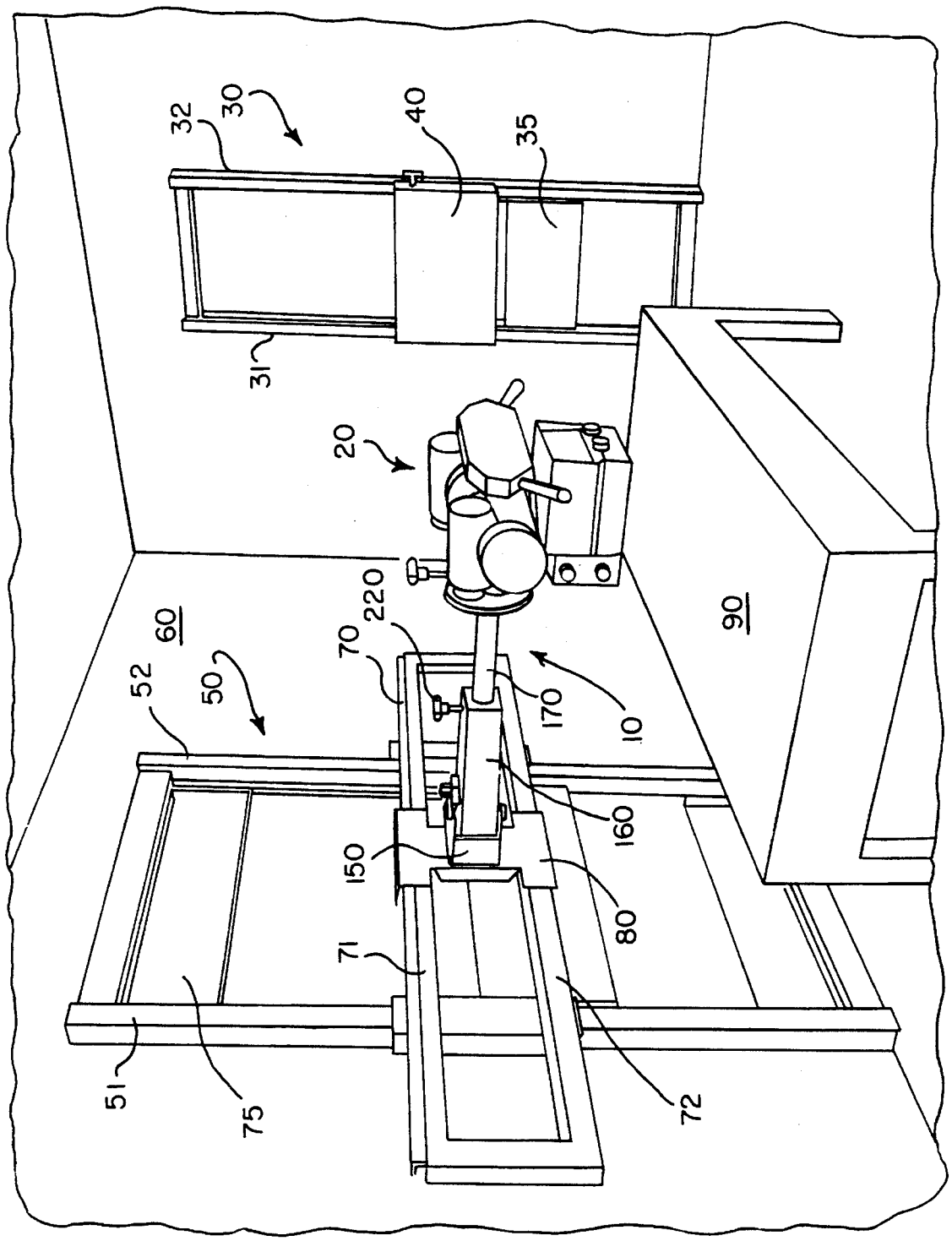
FIG. 1 is a perspective drawing of a preferred embodiment of the operating system and mounting assemblies of the subject invention showing a film stand, a source stand, a mounting assembly for the source, and the environment in which the system is used.

FIG. 1 shows a representative embodiment and the environment of use of the source assembly according to the invention. The source assembly is indicated generally by reference numeral 10. An X-ray source 20 is mounted to the source assembly 10, which provides various ranges of motion and support to the source 20. The source 20 and the source assembly 10 are shown in a representative X-ray environment. That environment includes a first stand 30 which serves as a film stand. Film stand 30 includes side rails 31 and 32. Reciprocable vertically along siderails 31 and 32 is a film carrier 40, which may illustratively receive an X-ray film cassette. Stand 30 also advantageously includes a counterweight 35 as disclosed in co-pending 07/850,891 now U.S. Pat. No. 5,469,492. A second stand 50 is also included. This stand is mounted to a wall 60 which defines a reference plane of interest to the description of this invention. Stand 50 includes side rails 51 and 52. Vertically reciprocable along siderails 51 and 52 is a first carriage 70. In turn, a second carriage 80 is horizontally reciprocable along the first carriage 70 which includes rails 71 and 72. Stand 50 also advantageously includes a counterweight 75 as disclosed in co-pending 07/850,891 now U.S. Pat. No. 5,469,492. Through the combination of stand 50, carriage 70 and carriage 80, the X-ray source 20 can be moved to a variety of positions in a plane parallel to the plane of the wall 60. It should be noted that alternative means for moving the X-ray source 20 in this plane could also be used. For example, the above-described prior art system including a vertical column with a carriage vertically moveable thereon, and a floor-track for horizontal movement of the column could be used. One skilled in the art will appreciate that other means for supporting and moving the X-ray source 20 in a plane parallel to the plane of the wall 60 are available.

The environment in FIG. 1 also includes a radiographic table 90. In a similar manner to stand 30, radiographic table 90 includes a means for receiving a film cassette, which is typically disposed underneath the top surface of the table 90.

Figure 5:
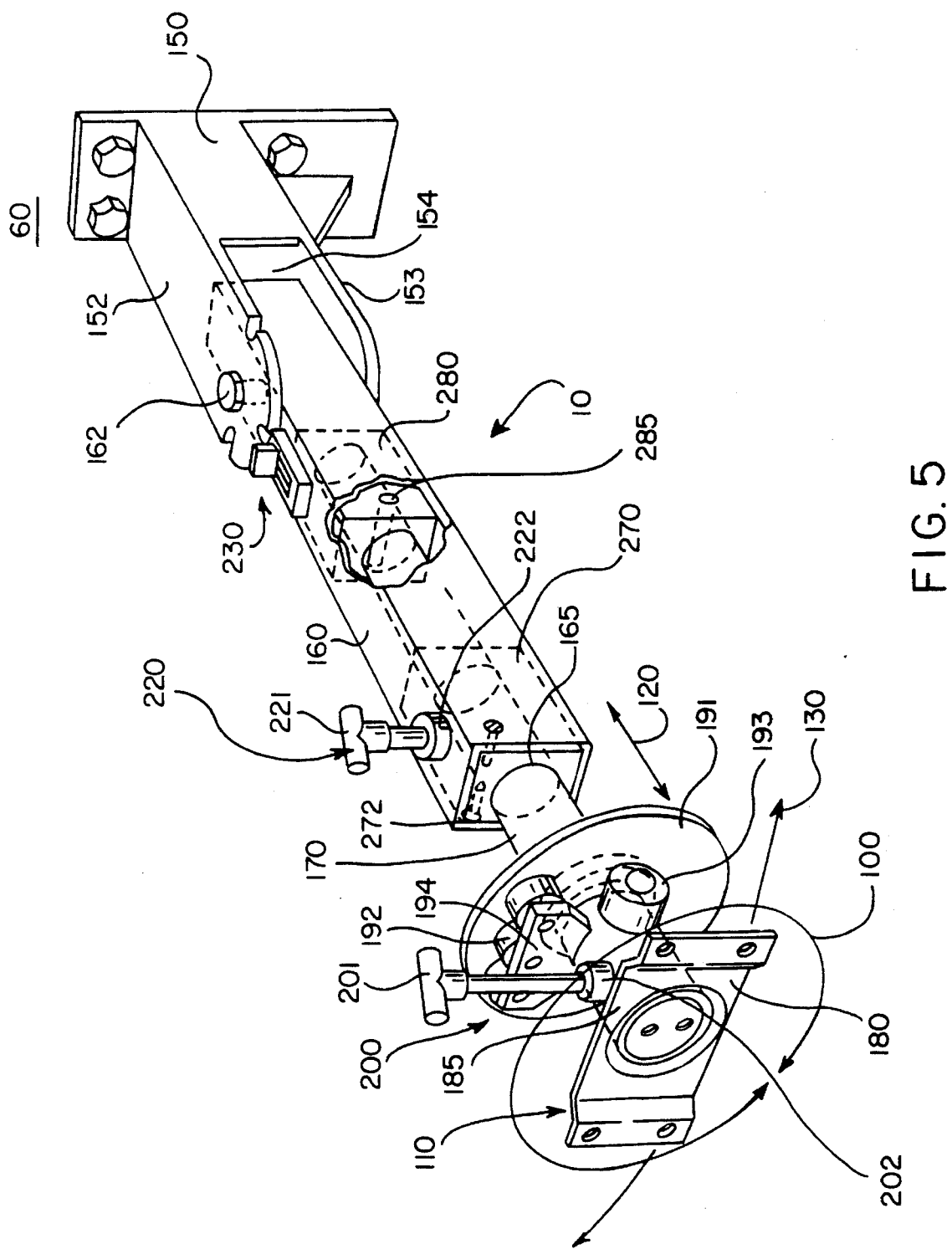
FIG. 5 is a perspective view of the source assembly according to this embodiment.

With the environment of use thus established, reference is now made to FIG. 5 which shows the various ranges of motion provided to the X-ray source 20 by means of the source assembly 10. Source assembly 10, according to the invention, offers three ranges of motion. The first range of motion, depicted by reference number 100 is rotational motion about a horizontal axis. As will be discussed in greater detail below, a source mounting 110 is mountable to the source 20. This source mounting 110 is pivotable about a horizontal axis, thereby allowing the source 20 to be rotated between a position wherein the X-ray beam is aimed at the floor, and a position wherein it is aimed at a wall. Returning briefly to FIG. 1, it can be seen that this is advantageous in that the source 20 may be used either for taking X-rays of a patient disposed on a radiographic table 90, or of the patient standing in front of the X-ray stand 30.

The second range of motion made available by source assembly 10 is the reciprocable motion depicted by reference number 120. This motion is motion away from and toward the wall 60 serving as a reference point in this description. By means of such reciprocable motion, X-ray's may be taken of a stationary patient at varying distances from the wall 60. Since previous source mounting systems have not included such movement relative to the wall 60, the same images could be obtained only by moving the patient relative to the X-ray source. Such patient movement is no longer required with the source assembly 10 according to the invention.

The third range of motion offered by source assembly 10 is depicted by reference numeral 130. This motion is essentially a pivoting motion in a horizontal plane. When the source is pivoted in this plane, it can be folded back to a position where it is adjacent to either the wall 60, or to other components mounted on that wall. Such a position may be particularly advantageous in that the X-ray source 20 can be removed as an obstacle from the room, while still maintaining all the other advantageous functional features offered by source assembly 10.

Figure 4:
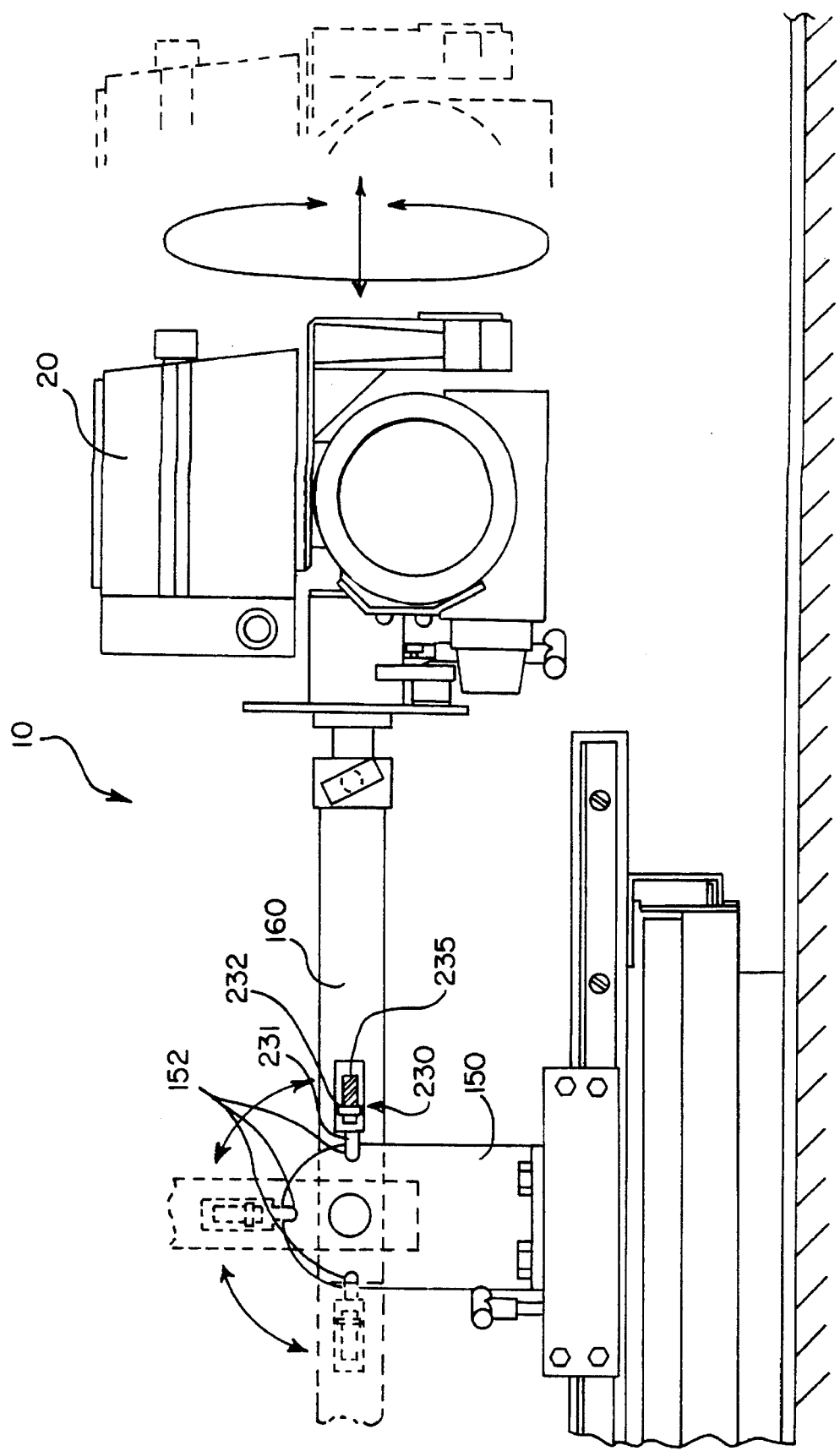
FIG. 4 is a top plan view showing the various ranges of motion of the source assembly.

In continuing reference to FIG. 5, the various components which provide for the advantageous ranges of motion can be seen. These components include a base member 150. Base member 150 is illustratively mounted to a carriage moveable on a stand, as seen in FIG. 1. The base member 150 horizontally projects away from that carriage, and away from the mounting wall 60. Member 150 includes a top plate on 152 and a bottom plate 153, and includes an open interior space 154. A tubular member 160, which in this embodiment has a square cross-section is pivotally mounted to base member 150 by means of pivot pin 162. The proximal end of tubular member 160 is received within opening 154 in the base 150. Opening 154 thus allows tubular member 160 to pivot about the pivot point 162. Tubular member 160 serves to extend the distance between the X-ray source, and the wall 60. This extension away from wall may become an obstacle under certain circumstances, and accordingly the tubular member 160 is pivotable about pivot point 162 to a position wherein X-ray source 120 is adjacent the wall 60. Such a position of tubular member 160, and X-ray source 120 is shown in FIG. 4.

Returning to FIG. 5, further extension of source 20 away from wall 60 is provided by means of a stem 170. Stem 170 is journalled within an interior passage way 165 within tubular member 160 for reciprocable motion with respect thereto. Thus, the distance of source 20 from wall 60 may be adjusted by means of adjusting the relative position of stem 170 and tubular member 160.

Rotational motion about a horizontal axis is provided to source 20 by means of source mounting 110. In addition to a face plate 180 for mounting to the X-ray source, source mounting 110 also includes a cylindrical collar 185. The cylindrical collar is journalled over the distal end of stem 170, to provide rotational motion with respect thereto.

Figure 6:
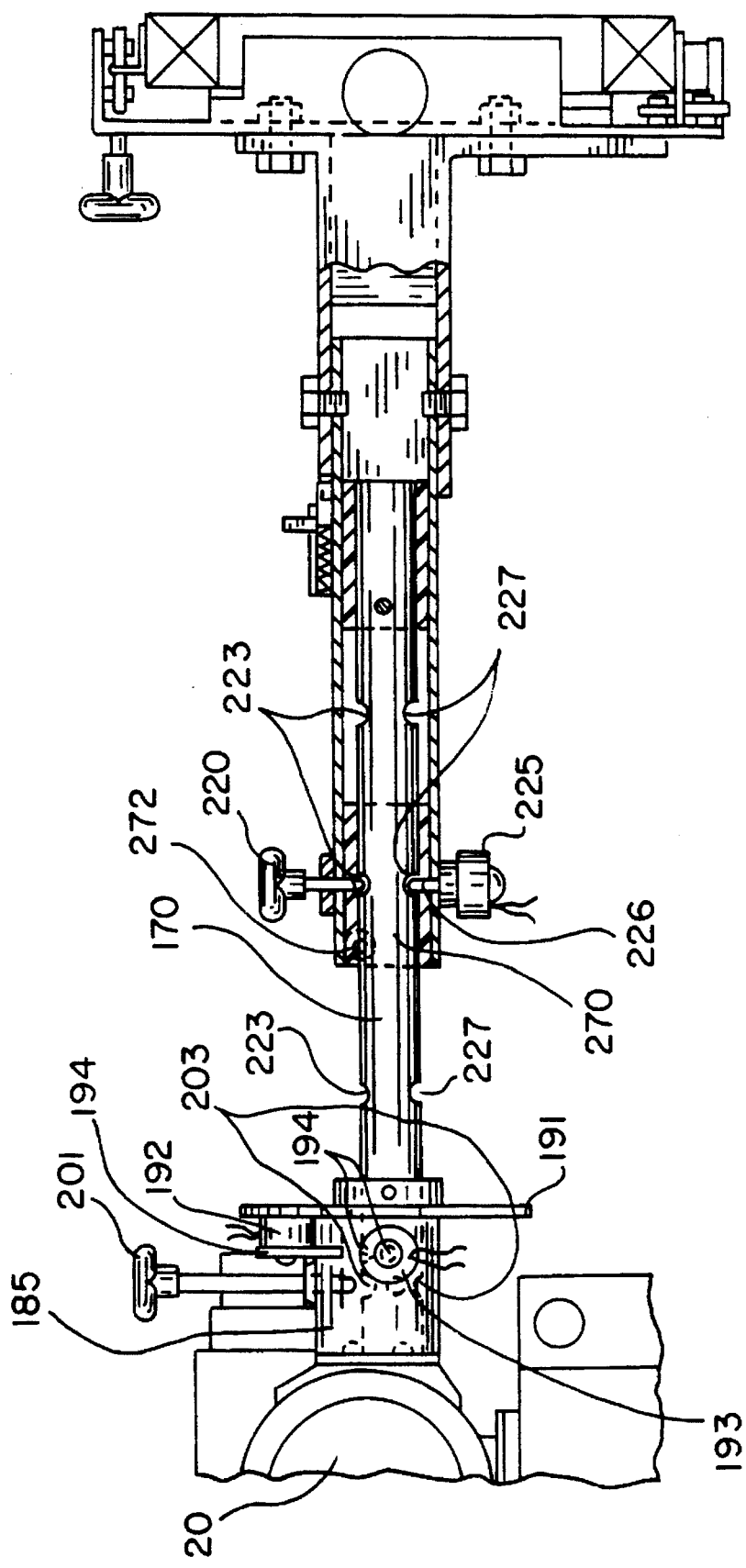
FIG. 6 is a side section view showing further detail of the source assembly according to the invention.

To provide for a reliable fixing of the source 20 at a variety of positions, source assembly 10 includes a position retaining system. Each range of motion of source assembly 10 has its own latch or other position-retaining device associated with it. In reference to FIG. 5, for the range of motion 100, a three component position retention assembly 200 is used. Assembly 200 first includes a T-shaped handle 201. T-shaped handle 201 is threaded and received within a threaded collar 202 by means of rotation of the handle 201, the distal end of T-shaped member 201 engages one of several angularly spaced detents 203 in stem 170 as shown in FIG. 6, thus preventing collar 185 from being able to rotate on stem 170. A spring loaded, electrically actuable solenoid 193 is also part of assembly 200. Solenoid 193, also shown in FIG. 6 includes a central spindle biased into engagement with a series of angularly spaced detents 194. Electrical actuation of solenoid 193, by means of a switch (not shown) pulls the spindle out of engagement with detents 194 to allow rotation of the collar 185 stem 170. Since both solenoid 193 and T-shaped handle 201 engage detents on stem 170, both must be disengaged to provide for rotation of collar 185. Typically, solenoid 193 is first energized to release the spindle from detents 194. The operator then unscrews T-shaped handle 201 and uses the T-shaped handle as a gripping point for rotating source 20. As an alternative the end of handle 201 could be spring biased into engagement with detents 203, instead of threaded in.

The third component of assembly 200 is a magnetic clutch. Three magnets 192 are mounted on a support 194 fixed to collar 185. A clutch plate 191 is fixed to stem 170. Engagement of magnets 192 with clutch plate 191 prevents unrestrained rotation of collar 185 about stem 170 when both solenoid 193 and T-shaped handle 201 are disengaged. Rather, the magnetic clutch offers smooth rotation of collar 185 between positions.

Similarly, the range of motion in FIG. 5 depicted by reference numeral 120 is controlled by means of assembly 220. 220 includes a T-shaped handle 221 which is threaded at its distal end and received within a threaded collar 222. Rotation of T-shaped handle 221 causes engagement of the distal end of member 221 with one of a plurality of longitudinally spaced detents 223, in stem 170 (FIG. 6), thus locking it against further horizontal reciprocation within tubular member 160. Alternatively, handle 220 may be spring—biased as opposed to threaded into engagement with detents 223. A spring loaded solenoid 225 also controls the reciprocating movement of stem 170. Solenoid 225 includes a spindle 226 biased by a spring into engagement with detents 227 spaced in stem 170. Actuation of solenoid 225 by a switch (not shown) causes spindle 226 to disengage detents 227. As with assembly 200, electrical solenoid 225 is typically first actuated to disengage spindle 226 from detents 227. Thereafter, the operator can manually disengage handle 220 from detents 223 to allow movement of the stem 170.

The range of motion indicated by reference numeral 130 in FIG. 5 is restricted by means of an engageable latch mechanism 230 the operation of which can be better understood by reference to FIG. 4. Base member 150 includes receiving notches 152. Although only three receiving notches 152 are shown in the present embodiment, any plurality of such notches could be used. Latch mechanism 230 includes a horizontally disposed latch member 231 which selectively engages in a receiving notch 152 to lock tubular member 160 in a given orientation. Movement of the latch member 231 is controlled by a finger tab 232. To positively lock latch 230 into position, latch member 231 is biased into engagement with slots 152 by means of a coil spring 235 which surrounds the stem of latch member 231.

Source assembly 10 also includes means for insuring smooth operation of the apparatus as source 20 is moved through the various ranges of motions provided by source assembly 10. In reference to FIG. 5, the smooth nature of the reciprocal movement of stem 170 with respect to tubular member 160 is provided by complimentary blocks, illustratively formed of nylon, and designated by reference numerals 270 and 280. Each block 270, 280 includes a central circular cross-sectional recess for receiving circular stem 170. Moreover, each block 270, 280 is journalled for sliding movement relative to the interior surface of tubular member 160. While block 270 is so journalled, it does not move with respect to 160. Rather, it is fixed in place at the distal end of tubular member 160 by means of screws 272. In reference to FIG. 6, it can be seen that block 270 also includes through-passages which allow access by the latching mechanisms to detents 223 and 227, respectively. Returning to FIG. 5, it can be seen that rear block 280 is adapted for slidable movement within tubular member 160. Stem 170 is fixed within the central hole in block 280 by means of a pin 285. Thus, as stem 170 moves outward in the sense of FIG. 5, block 280 slides outwardly along with it. The snug journalling of block 280 within tubular member 160 insures smooth and well supported motion of the stem 170 in both outward and inward directions. Blocks 280 and 270 also combine to present a limit to the outward motion of stem 170. When the front face of block 280 engages the rear face of block 270, further outward movement of the stem 170 is prevented.

Smooth operation of source assembly 10 is also facilitated by the magnetic clutch mechanism previously described. Magnets 192 engage a circular plate 191 to prevent sudden rotational movement of mounting 110 after solenoid 193 and handle 201 are disengaged from the stem 170.

Similarly, vertical movement of the source 20 is made smoother and less jerky by inclusion of the counter weight 75 shown in FIG. 1 and previously discussed. Overall, the functioning of source assembly 10, and the carriages to which it is attached, provide a smooth and reliable operation and movement without the need for undue exertion on the part of the operator.

The ranges of motion provided to source 20 by means of the source assembly 10 allow a wider variety of X-ray images to be taken by a single X-ray source. In the environment view of FIG. 1, the source 20 is shown directed toward the top of a radiographic table 90. Various images of a patient reclining on table 90 could be taken by taking advantage of the various ranges of motion provided for by assembly 10. Moreover, by rotation of the source 20 about a horizontal axis, the source could be directed at stand 40, for the purpose of taking an X-ray of a standing patient in that position.

Figure 2:
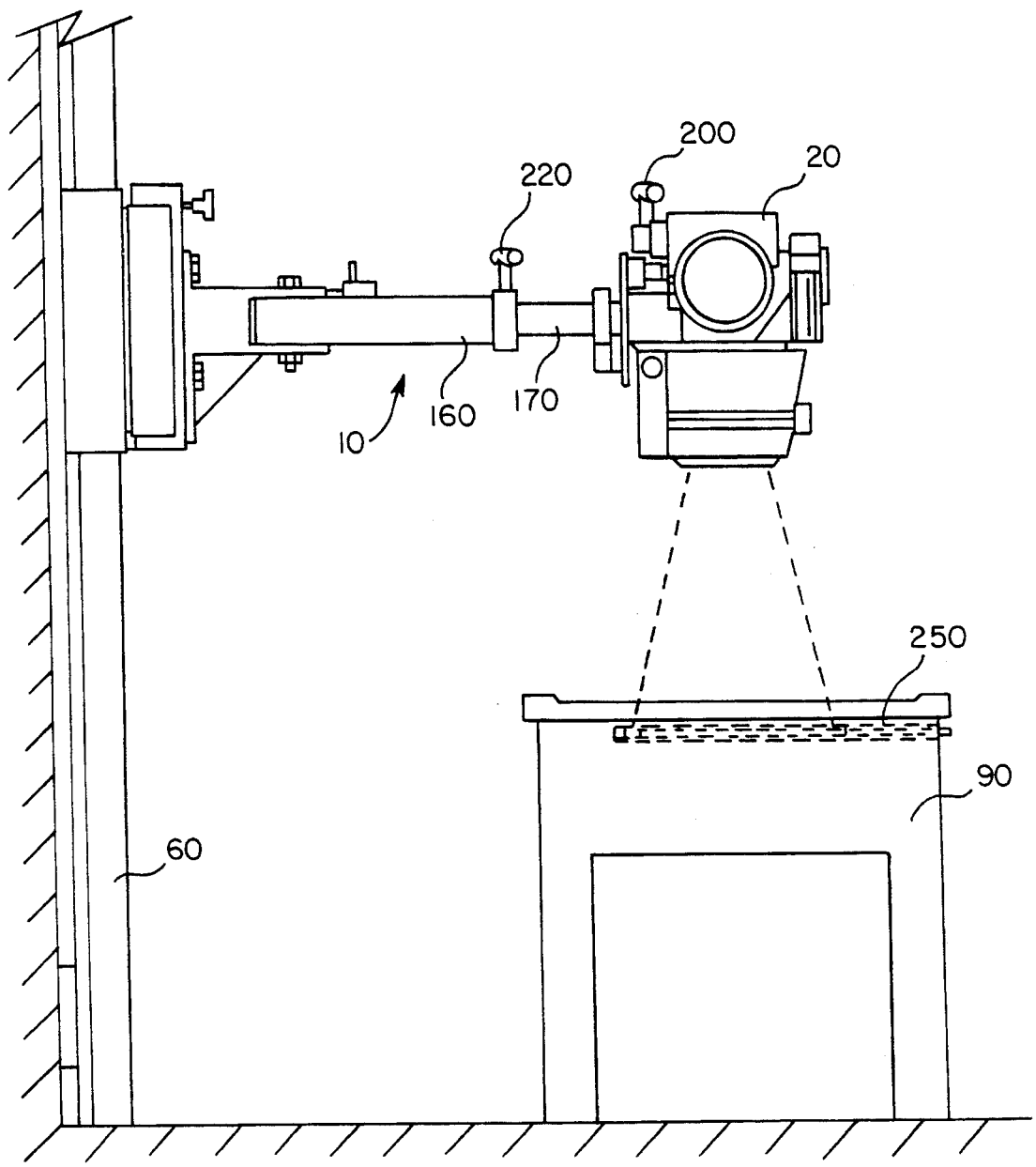
FIG. 2 is an elevational view showing one position of the source assembly.

FIG. 2 shows an elevational view of the position of source 20 as shown in FIG. 1. FIG. 2 also shows the location of the X-ray film cassette 250 as is necessary for taking X-ray images of a patient reclined on radiographic table 90.

Figure 3:
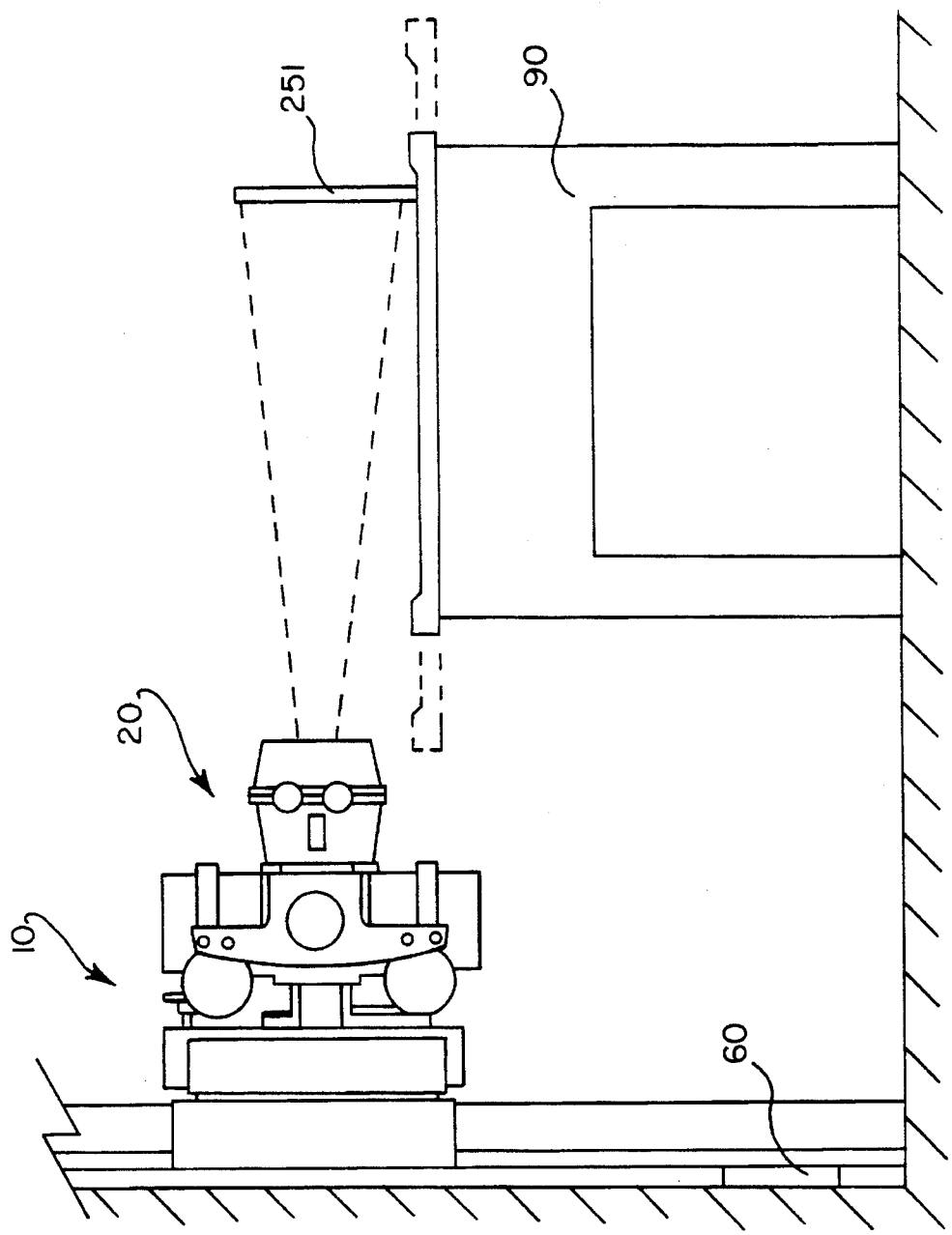
FIG. 3 is a further elevational view showing another position of the source assembly.

FIG. 3 shows an alternative position for source 20, made possible by means of the source assembly 10. In the position of FIG. 3, the source assembly has been rotated in the horizontal plane so that it is in the position shown in the plan view of FIG. 4 wherein the source is disposed adjacent to the wall 60. At the same time, source 20 is rotated so that the X-rays are emitted from the source 20 in a path roughly parallel to the floor. Accordingly, a film stand 251 may now be placed on radiographic table 90. This would allow, for example, X-ray of an arm resting on the top surface of radiographic table 90. Advantageously, this X-ray may be taken with the patient seated near the table, as opposed to having to be taken with the patient either standing or reclining on the table 90.

It will be appreciated by one skilled in the art that the ranges of motion provided by source assembly 10, according to the invention, make possible the taking of X-rays at a variety of positions which were not available by previous designs. Further, various modifications to the disclosed source assembly 10 will be apparent to those skilled in the art. All such modifications and equivalents are considered to be included in the scope of the invention as defined by the following claims.

What is claimed is:

1. An apparatus for supporting an X-ray source in a space, said space defined by a floor and at least one wall arranged substantially perpendicular to said floor, the X-ray source used for exposing patients to X-ray radiation, the apparatus comprising:

an upright support member mountable adjacent to said wall;

a slidably movable carriage supported by the support member and slidable thereto for planar movement in a vertical plane substantially parallel to said wall;

a source assembly mounted to the slidable carriage, and adapted to receive the X-ray source, the source assembly including:

a horizontally projecting base member fixedly mounted to the carriage;

a horizontally extending tubular member pivotably mounted to the base member for selective and fixedly positionable rotational motion in a horizontal plane substantially parallel to said floor;

a stem receivably journalled within the tubular member for horizontal telescoping reciprocation with respect thereto; and a source attachment fixedly attached to the X-ray source and including a collar journalled around the stem to provide rotational movement in said vertical plane about the stem.

2. The apparatus of claim 1, wherein the support member is slidably carried by a wall-mounted frame for movement in a vertical direction, and the carriage is slidably mounted on the support member for movement in a horizontal direction.

3. The apparatus of claim 2, wherein a counterweight system is attached to the support member.

4. The apparatus of claim 1, wherein the tubular member is pivotably mounted to the base member at a pivot point, the tubular member being pivotable between position's where it is parallel to said wall, and a position where it is perpendicular to said wall.

5. The apparatus of claim 4, wherein the tubular member is held in the positions by a latch, the latch including a horizontally disposed latch member movable relative to the tubular member, the base member including receiving notches for receiving the latch member and securing the tubular member in place.

6. The apparatus of claim 5, wherein a spring biases the latch member into engagement with the receiving notches.

7. The apparatus of claim 1, wherein a set of blocks are disposed within the tubular member, the blocks including central openings for receiving the stem, a first of said blocks being fixed to the stem and slidable within the tubular member upon movement of the stem, a second of said blocks being stationary within the tubular member and providing a positive stop to motion of the stem.

8. The apparatus of claim 1, wherein the stem includes longitudinally spaced detents, and the tubular member includes a manually actuable handle for engaging the detents and preventing motion of the stem.

9. The apparatus of claim 8, wherein the tubular member also includes an electrically actuated solenoid, the solenoid including a spindle engageable with the detents in the stem, a spring biasing the spindle into engagement with the detents, actuation of the solenoid withdrawing the spindle from the detents.

10. The apparatus of claim 1, wherein the stem includes angularly spaced detents, and the source attachment includes a manually actuable handle for engaging the detents and preventing rotation of the source attachment.

11. The apparatus of claim 10, wherein the source attachment also includes an electrically actuable solenoid, the solenoid including a spindle engageable with the detents in stem to prevent rotation of the source attachment, a spring biasing the spindle into engagement with the detents, actuation of the solenoid withdrawing the spindle from the detents.

12. The apparatus of claim 1, wherein a magnetic clutch is disposed between the stem and the source attachment, the magnetic clutch comprising a circular plate fixed to the stem, and at least one magnet fixed the source attachment and engageable with a face of the circular plate, the magnetic clutch preventing unrestrained rotation of the source attachment on the stem.

13. An apparatus as claimed in claim 1, wherein the tubular member is square in cross-section.

14. An apparatus as claimed in claim 13, wherein the stem is circular in cross-section.

* * * * *